United States Patent [19]

McMahon

[11] Patent Number: 4,823,473
[45] Date of Patent: Apr. 25, 1989

[54] EXTENSOMETER FOR MATERIAL TESTING MACHINE

[75] Inventor: Stephen M. McMahon, Quincy, Mass.

[73] Assignee: Instron Corporation, Canton, Mass.

[21] Appl. No.: 14,809

[22] Filed: Feb. 13, 1987

Related U.S. Application Data

[63] Continuation-in-part of Ser. No. 909,272, Sep. 19, 1986, abandoned.

[51] Int. Cl.$^4$ ................................................ G01B 5/00
[52] U.S. Cl. ...................................................... 33/787
[58] Field of Search ................. 73/826, 781, 734, 782, 73/760, 763, 774, 780; 33/147 D, 148 D, 148 R, 149 J, 150, 148 H, 148 E, 172 B

[56] References Cited

U.S. PATENT DOCUMENTS

| | | | |
|---|---|---|---|
| 2,545,482 | 3/1951 | Manjore et al. | 33/148 D |
| 2,578,066 | 12/1951 | Hyde | 33/148 D |
| 2,969,597 | 1/1961 | Lroshier | 33/172 B |
| 3,729,985 | 5/1973 | Sikorra | 33/147 D |
| 3,776,030 | 12/1973 | Strimel | 73/855 |
| 3,803,905 | 4/1974 | Wolf et al. | 73/763 |
| 4,098,000 | 7/1978 | Egger | 33/148 D |

FOREIGN PATENT DOCUMENTS

| | | | |
|---|---|---|---|
| 1084938 | 7/1960 | Fed. Rep. of Germany | 73/826 |
| 0110866 | 8/1974 | Japan | 33/147 D |
| 118670 | 4/1947 | Sweden | 33/148 E |
| 0715922 | 2/1980 | U.S.S.R. | 33/148 D |
| 0879385 | 11/1981 | U.S.S.R. | 73/857 |

OTHER PUBLICATIONS

Raske et al., "An Extensometer for Low Cycle Fatigue Tests on Anistropic Materials at Elevated Temperatures", J. Phys. & Sci. Instrum., vol. 12, 1979.

Primary Examiner—Michael J. Tokar
Assistant Examiner—Robert R. Raevis

[57] ABSTRACT

An extensometer for measuring strain in a materials test speciment including a frame, a pair of arms each having one end for contacting a portion of the specimen and a remote end, and a noncontact sensor assembly mounted on the arms to measure change in distance between the contact ends, the arms being pivotally supported between the ends by the frame at the centers of gravity of the arms and attached components of the sensor, to permit the arms to be freely pivotal.

12 Claims, 2 Drawing Sheets

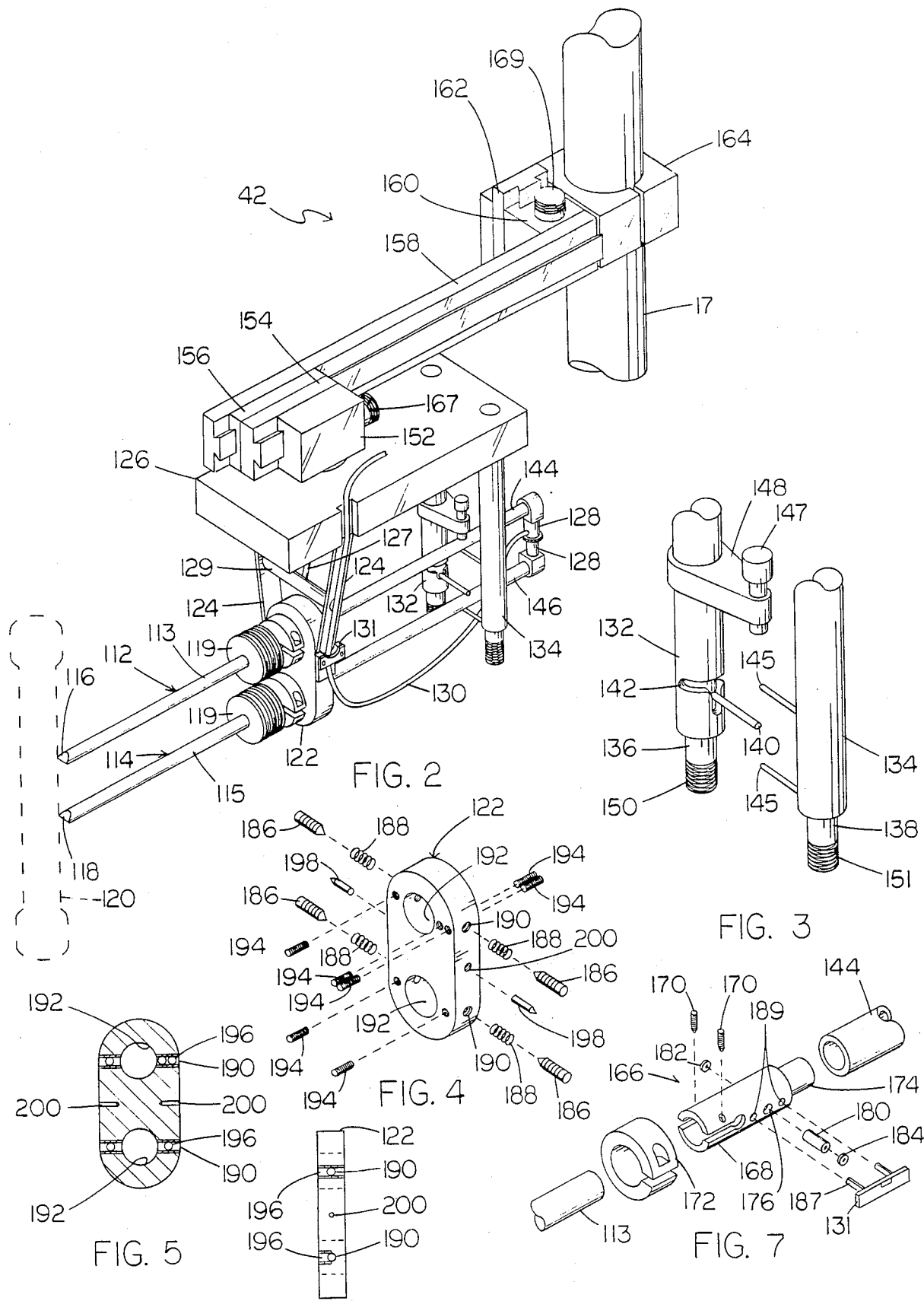

EXTENSOMETER FOR MATERIAL TESTING MACHINE

This application is a continuation-in-part of my copending application of the same title, Ser. No. 909,272 filed Sept. 19, 1986 now abandoned, and assigned to the assignee hereof.

FIELD OF THE INVENTION

The invention relates to extensometers used with material testing machines.

BACKGROUND OF THE INVENTION

In the prior art, there have been strain measuring extensometers utilizing arms connected to a strain gaged flexural element sensor. However, these devices generally require significant specimen contact forces to eliminate slipping of the arms caused by the spring force of the flexural elements.

SUMMARY OF THE INVENTION

It has been discovered that an extensometer can be provided with arms that are less likely to slip (even on ceramic surfaces) and do not require a high normal force by providing noncontact sensors (in particular capacitive sensors) to sense the distance between the contact ends of the arms and pivotally connecting two arms near the centers of gravity of the arms and attached sensor components.

In preferred embodiments the arms are pivotally connected to a frame which is also pivotally supported (to provide even contact of the knife edges with the sample); the arms are supported using pivot screws that engage plates that are mounted in a passage through the arm and are capable of slight deflection, they provide firm pivotal mounting of the arms even with changes in the compression provided by pivot screws; the orientation of the knife edges with respect to each other is adjusted by four adjustment screws that locate a pivot screw; the pivot screws are threaded within helical screw thread inserts received in holes through the frame; the frame is pivotally supported by arms that are spring-biased (with adjustable force) toward the sample; signal cables to the capacitive sensor pass through the axes of pivoting of the arms to reduce bending of the wire and resulting friction; the initial distance beween the knife edges ("gage length") is set by adjustable stops that are moved into position above the ends of the arms near the sensor ends and spring retaining members that are moved into position below the ends of the arms (this allows the two arms to move in the longitudinal axis while maintaining the gage length); and the entire extensometer support is mounted for sliding toward the sample.

Other advantages and features of the invention will be apparent from the following description of a preferred embodiment thereof and from the claims.

DESCRIPTION OF THE PREFERRED EMBODIMENT

The preferred embodiment will now be described.

DRAWINGS

FIG. 2 is a perspective view of an extensometer assembly.

FIG. 3 is a perspective view of a gage-length adjustment mechanism of FIG. 2 extensometer.

FIG. 4 is an exploded perspective view of a pivotal frame for arms of the FIG. 2 extensometer.

FIG. 5 is a vertical sectional view of FIG. 4 frame.

FIG. 6 is a side elevation of the FIG. 4 frame.

FIG. 7 is an exploded perspective view of the connecting body and related components of an arm of the FIG. 2 extensometer.

STRUCTURE

Figure 1:
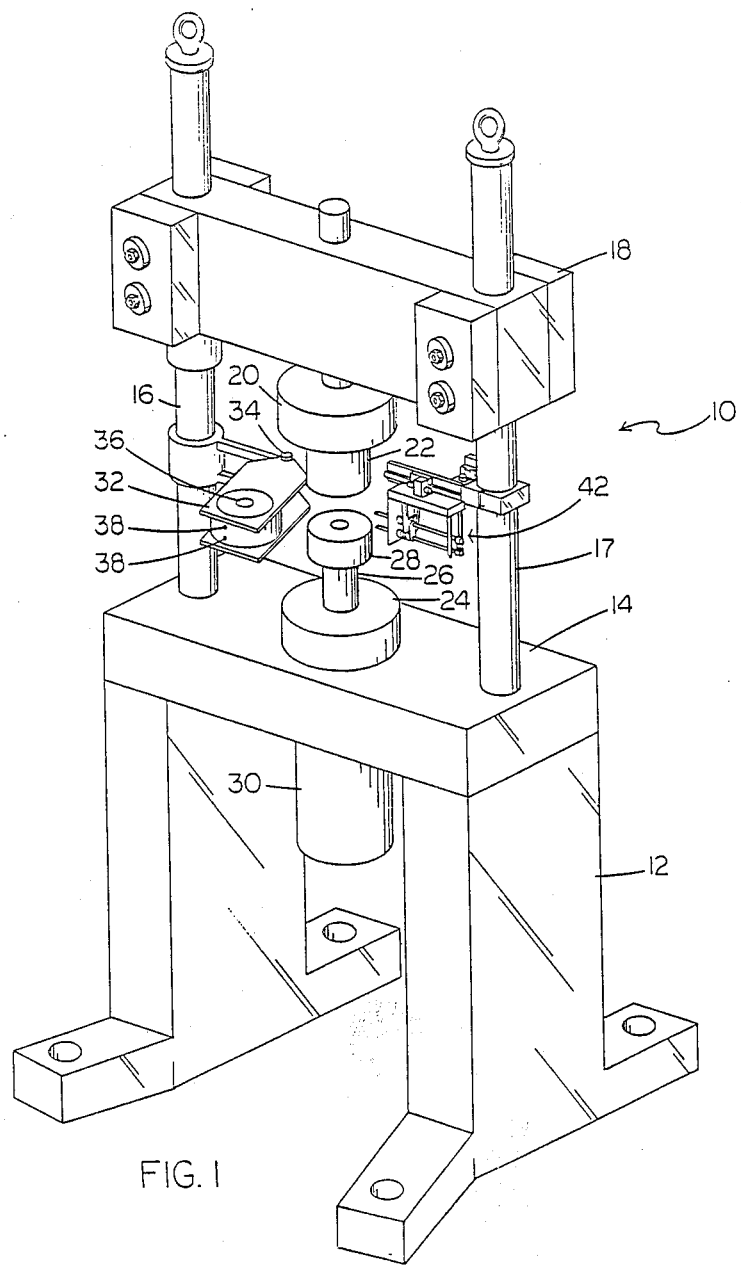
FIG. 1 is a perspective view of a material testing load frame according to the invention.

Referring to FIG. 1, there is shown material testing load frame 10 including feet 12, table 14, vertical columns 16, 17 extending upwardly from table 14, and crosshead 18 between columns 16, 17. Connected to crosshead 18 are load cell 20 and upper grip 22, for gripping the upper end of a sample under test. Directly therebelow and supported by table 14 are hydrostatic bearing 24, actuator rod 26, and lower grip 28, for gripping the lower end of a sample. Actuator 30 is supported below table 14 and drives rod 26, which passes through a hole through table 14. Supported on column 16 is 1500° C. furnace 32, which is pivotally mounted about pivot 34 so as to be movable from the standby position shown in FIG. 1 to an operating position between grips 22, 28. Furnace 32 has central bore 36 for receiving the elongated sample under test and two horizontal passages 38 leading to bore 36 for receiving fingers 112, 114 (FIG. 2) of extensometer assembly 42, supported by column 17.

Referring to FIG. 2, there is shown extensometer 42 supported on column 17. Extensometer 42 includes two arms 112, 114 including solid alumina members 113, 115 and hollow alumina rear extensions 144, 146. Solid members 113, 115 have knife-edge contact ends 116, 118, contacting ceramic sample 120 (shown in phantom), and air cooling fins 119. Arms 112, 114 are pivotally connected at their centrally located bodies to frame 122, itself pivotally supported by two flexural hangers 124 pivotally supported at their tops to sliding support 126. Hangers 124 are spring-biased toward sample 120 via two springs 127, mounted between support 126 and support 129, and biasing support 129 in a forward direction. At the remote ends of extensions 144, 146 is capacitive displacement sensor 128 (available from HiTech under the trade designation HPB-75-4-5-12-m), providing noncontact, zero-force measurements. The signal cables 130 of sensor 128 each passes through the clamp 131 connected to its respective arm for pivoting with it about its axis of rotation. Each arm 112, 114 is pivotally supported about the center of gravity of it and its attached component of sensor 128.

Extending downward from sliding support 126 on opposite sides of arms 112, 114 are vertical, hollow housings 132, 134, containing within them rotatable bodies 136, 138, which are spring-biased downward and upward, respectively, by internal springs (not shown). Body 136 carries transverse dowel pin 140 passing out of L-shaped passage 142 so that pin 140 can be rotated into and out of position directly above rear extension 146. Body 138 similarly has two cantilevered spring members 145 extending transversely and passing through horizontal slots (not shown) of housing 134 for rotation into position and out of position below extensions 144, 146. Threaded micrometer adjustment 147 is mounted on horizontal clamp 148 on housing 132. Bodies 136, 138 include knurled knobs 150, 151 extending from the bottom of housings 132, 134.

Attached to the upper surface of sliding support 126 are dovetail slides providing fine and coarse horizontal sliding of support 126. Directly attached to the upper surface of support 126 is fine horizontal control saddle 152 having a female dovetail track therein receiving the slidably mating male member of base 154. Base 154 is in turn fixedly secured to saddle 156, mating with coarse adjustment base 158, which is attached by mating vertical adjustment saddle 160 and base 162 to column clamp 164, mounted on vertical column 17 of the testing load frame 10. Knob 167 on saddle 152 provides fine horizontal movement of saddle 152 relative to base 154, and knob 169 on saddle 160 provides fine vertical adjustment of saddle 160 relative to base 162. Clamp 164 acts as a mounting assembly; support 126 and frame 122 carried by it are thus slidably mounted with respect to it, and there is a vertical position adjustment mechanism (saddle 160, base 162) between clamp 164 and support 126.

Referring to FIGS. 4–7, the pivotal support of arms 112, 114 is shown in more detail. Referring to FIG. 7, the ceramic extensometer rod 113 is connected to tubular extension 144 via body 166. The rear end of rod 113 is received in counterbored end 168 of body 166 and is rotationally adjusted and secured therein by set screws 170 and outer rod clamp 172. Tubular extension 144 fits over stud 174 on the other end of body 166. Within horizontal through-hole 176 (5.55+0.00-0.02 mm inner diameter) of body 166 are press-fit cylindrical spacer 180, and two press-fit flexible bearing disks 182 (one on each side of cylinder 180) having holes 184 receiving pointed ends of pivot screws 186 (FIG. 5). Spacer 180 has a 4.0 mm inner diameter and a 5.55+0.05-0.00 mm outer diameter outside of horizontal straight knurls. Bearing disks 182 are made from Precision Brand Products stainless steel shim 0.25 mm flat sheet (T302, cold rolled, full hard, RC about 40/45) and has a 5.55+0.02-0.00 mm outer diameter and a 0.50±0.1 mm inner diameter. Bearing disks 182, also referred to as plates, are sufficiently flexible to be capable of slight deflection, to provide firm pivotal mounting of arms 112, 114 even with changes in the compression provided by pivot screws 186. Extension 144 (FIG. 7) is inserted through opening 192 of frame 122 (FIG. 4) to obtain the structure shown in FIG. 2. Wire clamp 131 has pins 187 received in holes 189 in body 166 on opposite sides of through-hole 176.

Referring to FIGS. 4 to 6, pivot screws 186 have 60°±1° sharp pointed (0.08 mm max R) conical ends with an 8 microinch finish (for smoothness), and have M3x 0.5 mm pitch threads. Pivot screws 186 are threadedly received in helical screw thread inserts 188 within horizontal passages 190 of frame 122 leading to openings 192. Inserts 188 and pivot screws 186 are held in place by set screws 194 received in threaded passages 196. There are four set screws 194 and threaded passages 196 associated (two on each side) with one pivot screw 186 (the upper right-hand on in FIG. 4) in order to adjust the position of that pivot screw in a horizontal plane so as to adjust the position of arm 112 in that plane with respect to arm 114 below it so that they are both vertically aligned with each other. Frame 122 is pivotally supported by hangers 124 by pivot pins 198, mounted in holes 200 and having 45° conical pointed ends.

OPERATION

In operation, a ceramic sample 120 is loaded into frame 10 by first inserting it into bore 36 of furnace 32 while furnace 32 is in the standby position shown in FIG. 1. The heater and sample (wired with strain gages, not shown, at four locations around its midsection and two locations above and two locations below its midsection) are swung into position between grips 22, 28.

Cantilever spring members 145 and pin 140 are rotated into the position shown in FIG. 3, retaining rear extensions 144, 146 of pressure fingers 112, 114 between pin 140 and the lower spring member 145 and between micrometer 147 and the upper spring member 145. Micrometer 147 is then adjusted until the desired gage length is attained between knife edges 116, 118. The extensometer rods 112, 114 are then moved horizontally into position by pushing sliding support 126 toward sample 120 so that saddle 156 slides with respect to base 158. Fine horizontal adjustment is then made using knobs 167 until knife edges 116, 118 contact sample 120. Cantilever spring members 145, dowel pin 140 and micrometer 147 are then disengaged permitting arms 112, 114 to freely pivot in response to changes in length of sample 120.

The knife edges 116, 118 firmly maintain their positions on locations of sample 120 without a high normal force and without resistance to change in length owing to the noncontact zero-force nature of the capacitive sensor 128 and the freely pivotal mounting about the centers of gravity. By having cable wire 130 pass through the axis of pivoting of arm 112, it is not bent during movement of arm 112, and thus outside rotational forces on the arm are reduced.

OTHER EMBODIMENTS

Other embodiments of the invention are within the scope of the claims.

What is claimed is:

1. An extensometer for measuring strain in a specimen comprising
   a frame,
   a first arm having a contact end for frictionally contacting a first portion of a transverse surface of said specimen so as to move with said portion and a remote end, said first arm being freely pivotally supported about a first pivot axis between said ends by said frame, said first pivot axis passing through said first arm near the center of said first arm,
   a second arm having a contact end for frictionally contacting a second portion of said transverse surface of said specimen so as to move with said second portion and a remote end, said second arm being freely pivotally supported about a second pivot axis between said ends by said frame, said second pivot axis passing through said second arm near the center of said second arm,
   a noncontact sensor assembly having at least one component connected to a said arm at a portion that moves as said contact ends to measure change in distance between said contact ends, and
   a support,
   said frame being pivotally mounted with respect to said support to provide even contact of said contact ends with said sample.

2. The extensometer of claim 1 wherein said noncontact sensor assembly comprises a capacitive sensor attached to at least one said remote end.

3. The extensometer of claim 2 further comprising an electrical signal wire coupled to said component of said sensor assembly that is connected to pass through the axis of pivoting of the arm to which said component is attached to reduce outside rotational forces on the arms.

4. The extensometer of claim 1 wherein said frame is itself pivotally supported via hangers from said support.

5. The extensometer of claim 4 wherein said hangers are spring-biased toward said specimen.

6. The extensometer of claim 1 wherein said arms are pivotally connected to said frame via pointed screws that are mounted in said frame and engage apertures in plates mounted on said arms, said plates being sufficiently flexible to be capable of slight deflection, to provide firm pivotal mounting of the arms even with changes in the compression provided by the pointed screws.

7. The extensometer of claim 6 further comprising opposing adjustment set screws on said frame and bearing against opposite sides of a said pointed screw along an axis perpendicular to that of said last mentioned pointed screw to adjust the alignment of said last mentioned pointed screw and thus said arm.

8. The extensometer of claim 6 wherein said pointed screws are threaded within helical screw thread inserts received in holes in said frame.

9. The extensometer of claim 1 further comprising first and second stops that are each moved into position on one side (above or below) of the respective remote end of said first and second arms and first and second spring-retaining members that are moved into position on the other side (below or above) of the remote ends of said arms.

10. The extensometer of claim 1 further comprising a mounting assembly and wherein said frame is slidably mounted with respect to said mounting assembly along axes toward said sample.

11. The extensometer of claim 10 wherein said mounting assembly includes a fine and coarse horizontal motion adjustment mechanism.

12. The extensometer of claim 10 further comprising a vertical position adjustment mechanism between said mounting assembly and said frame.

* * * * *

UNITED STATES PATENT AND TRADEMARK OFFICE
CERTIFICATE OF CORRECTION

PATENT NO. : 4,823,473
DATED : April 25, 1989
INVENTOR(S) : Stephen M. McMahon and Joseph P. DeNicola It is certified that error appears in the above-identified patent and that said Letters Patent is hereby corrected as shown below:

Joseph P. DeNicola of Hingham, MA should also be listed as an inventor.

In the Abstract, line 2, "speciment" should be --specimen--;

Column 1, line 36, "they" should be --to--;

Column 2, line 45, "HiTech" should be --HiTec--;

Column 3, line 53, "0.5" should be --.5--;

Column 3, line 61, "on" should be --one--;

and

Column 4, line 60, after "ends" insert --move--.

Signed and Sealed this
Nineteenth Day of December, 1989

Attest:

JEFFREY M. SAMUELS

Attesting Officer     Acting Commissioner of Patents and Trademarks